United States Patent
Sorensen

(10) Patent No.: US 6,339,678 B1
(45) Date of Patent: Jan. 15, 2002

(54) METHOD FOR VAPORIZING AND SUPERHEATING A STERILIZING AGENT AND DEVICE THEREFOR

(75) Inventor: Karsten Sorensen, Griesheim (DE)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 09/367,067

(22) PCT Filed: Jan. 15, 1998

(86) PCT No.: PCT/EP98/00206

§ 371 Date: Oct. 8, 1999

§ 102(e) Date: Oct. 8, 1999

(87) PCT Pub. No.: WO98/34649

PCT Pub. Date: Aug. 13, 1998

(30) Foreign Application Priority Data

Feb. 7, 1997 (DE) .......................................... 197 04 639

(51) Int. Cl.[7] .......................... A01G 13/06; C10K 15/00
(52) U.S. Cl. ........................................ 392/386; 269/139
(58) Field of Search ................................ 392/386, 387, 392/390, 394, 396, 397, 398, 465, 466, 485; 261/139, 141, 142, DIG. 65; 422/26

(56) References Cited

U.S. PATENT DOCUMENTS

| | | | |
|---|---|---|---|
| 2,576,976 A | * 12/1951 | Stagner | ..................... 392/398 |
| 3,250,723 A | * 5/1966 | Fortney | ..................... 392/397 |
| 4,724,824 A | * 2/1988 | McCoy et al. | ............... 392/396 |
| 4,896,478 A | 1/1990 | Reiter | |
| 5,078,976 A | * 1/1992 | Schibauchi et al. | .......... 392/395 |
| 5,290,511 A | * 3/1994 | Newman | ..................... 422/26 |
| 5,949,958 A | * 9/1999 | Naperkowski et al. | ....... 392/399 |

FOREIGN PATENT DOCUMENTS

| | | |
|---|---|---|
| EP | 0 427 051 | 5/1991 |
| FR | 2 609 149 | 7/1988 |

* cited by examiner

Primary Examiner—Sang Paik
(74) Attorney, Agent, or Firm—Burns, Doane, Swecker & Mathis, L.L.P.

(57) ABSTRACT

A device and a method are described for vaporizing and superheating a sterilizing agent. The sterilizing agent is brought to a first temperature and vaporized with the aid of a heated surface. The vapor is subsequently bought to a second, higher temperature and super heated by means of heating elements. A heater, having super heating channels and heating elements, is connected after a vaporizing chamber. The sterilizing agent is sprayed onto the heated surface, which is heated to the first temperature. The first temperature is lower than the surface temperature at which film boiling begins. The first temperature of the heated surface is sensed and converted into signals for controlling the heating elements for super heating. This sterilizing agent vapor is heated in a counter flow such that the first temperature is kept substantially constant by means of the second, higher temperature and by means of a flow of heat directed in the opposite direction to the flow of vapor.

14 Claims, 3 Drawing Sheets

METHOD FOR VAPORIZING AND SUPERHEATING A STERILIZING AGENT AND DEVICE THEREFOR

Figure 1:
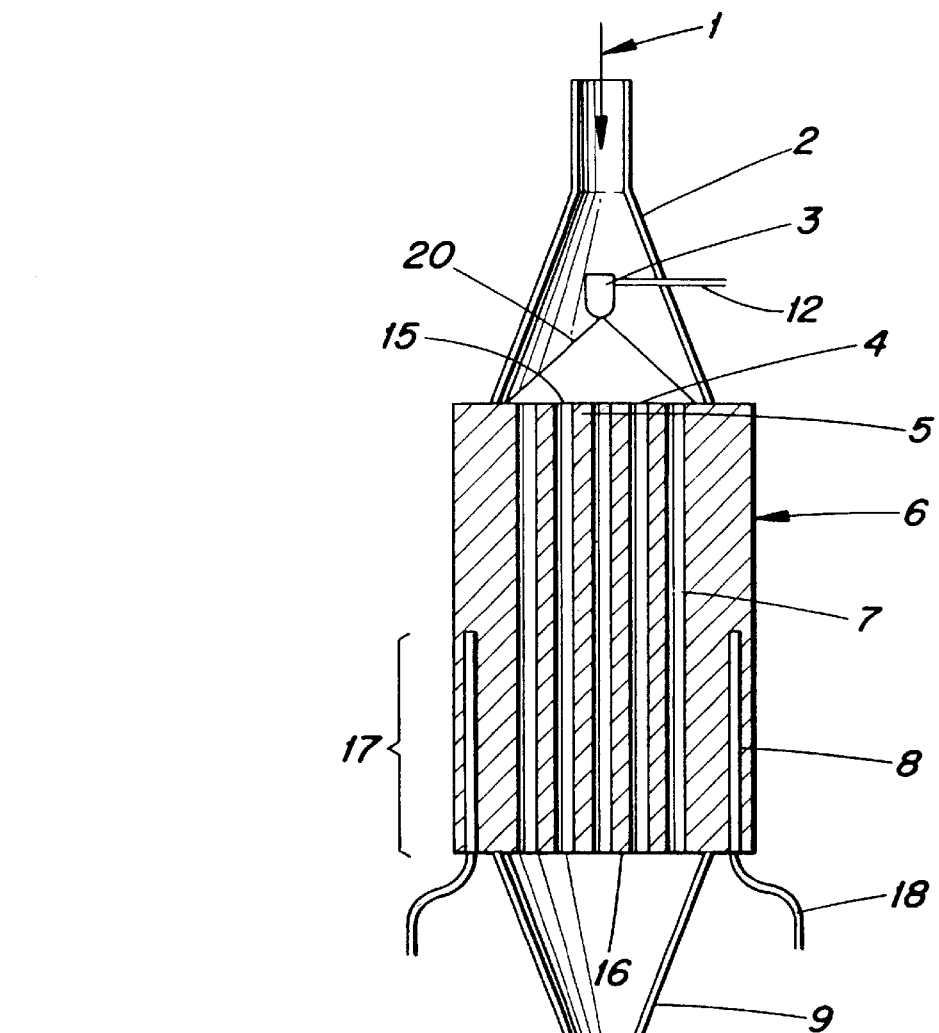

The invention relates to a method for vaporising and super-heating a sterilising agent, in which the sterilising agent is brought to a first temperature and vaporised with the aid of a heated surface, and the vapour is subsequently to brought a second, higher temperature and super-heated by heating elements.

The invention also relates to a device of this type, which is provided with a vaporising chamber and a heater with super-heating channels and heating elements connected after said vaporising chamber.

It is known to vaporise and to super-heat liquids, and in particular water, for many purposes. With this, moist vapour is produced in a first container or boiler by heating the liquid. The vapour is subsequently conducted into a second container or boiler which, without increasing pressure, super-heats the vapour, that is to say heats it above the boiling point of the liquid, so that the vapour leaving this boiler is super-heated and can be described as dry vapour.

There are various liquids similar to water which can be subjected to such methods, as required. For example, it is desirable from time to time to super-heat sterilising agent in order to apply it as super-heated vapour to surfaces to be sterilised. The known methods and devices for producing super-heated sterilising vapours have the disadvantage that they are expensive, require a relatively large amount of heat and can only be produced in devices which take up a large amount of space.

The object of the invention is therefore to simplify the known methods and make them more effective, and to use technically more simple and more compact components for the device.

With respect to the method, the solution of the object according to the invention is in that
a) the sterilising agent is sprayed onto the heated surface, which is heated to a first temperature,
b) which is lower than the surface temperature at which film boiling begins,
c) the first temperature of the heated surface is sensed and converted into signals for controlling the heating elements for super-heating, and
d) the sterilising agent vapour is heated in a counter flow such that the first temperature is kept substantially constant by means of the second, higher temperature and by means of a flow of heat directed in the opposite direction to the flow of vapour.

While with the known methods and devices for producing super-heated sterilising agents, the heated surface can be said to be the internal surface of the container in which the liquid is boiled, or, in the case of a boiler, is the internal surface of pipes on or in which the liquid to be heated and vaporised lies, in accordance with the invention, the sterilising agent is brought into contact with the heated surface by means of sprays. The solid mass of liquid therefore does not come into contact with the heated surface, but instead only a mist of sterilising agent, that is to say a large member of finely distributed droplets. In this way the active surface of the flowable sterilising agent is significantly increased, and the heat transfer from the heated surface to the respective liquid droplets is improved.

When the first temperature described of this heated surface is now lower than the surface temperature at which film boiling of the sterilising agent concerned begins, the total thermal balance is particularly advantageous for reasons which will be explained hereinafter. According to the method in accordance with the invention, a significantly smaller quantity of heat is needed for vaporising and super-heating the sterilising agent, and in this way energy can be saved. Because the temperature of the so-called heated surface is kept within the range described, a high thermal gradient is guaranteed and thereby a large flow of heat to the heated surface from the heater deliberately arranged at a distance from the heated surface.

This heating can be advantageously controlled and used for regulating the method according to the invention when a temperature sensor produces signals corresponding to the first temperature of the heated surface, with which the heating elements can be regulated for super-heating. In other words, a quantity of heat is constantly produced by the heating elements such that it flows towards the heated surface and keeps it at the temperature previously described.

The many small droplets of the initially flowable sterilising agent are vaporised on the heated surface, and this vapour flows, influenced by the pressure differential, in a direction which is counter to the direction of the flow of heat. In this way, the sterilising agent vapour is heated in a counter-flow by means of the novel method. Advantageously, the first temperature of the heated surface is maintained at the correct level by means of a second, higher temperature in the downstream area of the method, because the heat flow is produced counter to the direction of the flow of vapour. In this way the heated surface can be kept at the desired first temperature.

By means of the method according to the invention, the optimum temperature of the heated surface is obtained for vaporising the mist droplets of sterilising agent. It is very important to find the correct temperature of the heated surface, to set it and to keep it at the correct value during operation. From a diagram which will be explained hereinafter, it is evident that theoretically, given the optimum temperature of the heated surface, a relatively large amount of heat can be transferred from the heated surface to the mist droplets of sterilising agent. In operation, the applicant has previously carried out other experiments with other heating methods, and for example, attempted vaporisation and super-heating by means of hot air with different temperatures. The degree of effectiveness of such methods remains far below that according to the method according to the invention, however.

If now, by following the teaching according to the invention, a high degree of heat emission is obtained on the up-stream heated surface, large quantities of flowable sterilising agent can be vaporised per unit time. With correct adjustment of the heating elements, that is to say with a correct temperature of the super-heated vapour in the downstream area of the method, a significantly lower heat flow into the vapour is obtained so that the amount of heat produced by the heating elements flows towards the heated surface in the opposite direction of flow to the flowing vapour. In this way the optimum temperature can be established and maintained in a very simple manner.

When, in an advantageous embodiment of the invention, the sterilising agent is hydrogen peroxide, the vaporisation method can be carried out under conditions similar to those for water to good effect. Clearly, hydrogen peroxide at different concentrations can be used. Hydrogen peroxide has similar characteristics to water with respect to temperature, vaporisation and super-heating properties.

It has been shown advantageous for carrying out the method according to the invention when, in a preferred embodiment, the first temperature of the heated surface is kept in the range of 100° C. to 150° C., preferably in the range of 120° C. to 140° C.

If the amount of heat which can be derived from the surface of the sterilising agent, measured in watts per square meter, is plotted on a diagram above a temperature difference formed from the current temperature minus the boiling point of the sterilising agent, measured in degrees Celsius, a first maximum is found for water at a current temperature of approximately 130° C. At this temperature the maximum amount of heat can thus be transferred from the heated surface to the sterilising agent.

The relationships are quite different at temperatures of, for example, 200° C. If the sterilising agent vapour is super-heated to such a temperature using the method according to the invention, that is to say by the action of the heating element, the diagram shows a greatly reduced amount of heat which can be transferred to the sterilising agent. The amount of heat produced by the heating elements can, however, flow towards the heated surface because of the high heat consumption of said heated surface, whereby the heat flow previously described is produced.

It can be advantageous to use a different and additional measure in accordance with the invention with the novel method, which is characterised according to the invention in that a gaseous carrier medium is introduced into the spray stream of sterilising agent. Such a carrier medium could, for example, be air or another gaseous medium. The consumption of sterilising agent can be reduced when, for example, the concentration of the sterilising agent to be used finally does not need to be 100%, 80% or the like. The carrier medium can optionally be used as a propellant when it is introduced at a suitable flow speed, for example when it is blown into the spray stream of sterilising agent.

It is a further advantageous according to the invention when the gaseous carrier medium has a temperature in the range of 130° C. to 170° C., preferably of 120° C. to 160° C., and particularly preferably of approximately 150° C. When these temperatures are used for the carrier medium, a good degree of efficiency is obtained for hydrogen peroxide as a sterilising agent. On the one hand, dilution and/or optionally its propulsion is obtained, and removal of heat by it from the sterilising agent is prevented by the temperature of the carrier medium.

The object described hereinabove is solved according to the invention by means of the device in that a) the heated surface is the up-stream surface of the heater, b) onto which the vaporising chamber is directly mounted, c) a nozzle connected to a supply line leading to the exterior is fitted in the vaporising chamber, opposite the heated surface, d) open, continuous channels are provided from the up-stream surface to the down-stream end surface of the heater, and that e) the heating elements are housed in the down-stream end area of the heater.

With a vaporising device constructed in this way, the super-heating of the vaporised medium, for example a sterilising agent, can be done in a narrow space and with simple means. By arranging the spray nozzle opposite and up-stream of the heated surface, the liquid to be vaporised, for example the sterilising agent, is distributed in a mist of very fine droplets. Because the vaporising chamber is mounted directly on the up-stream surface of the heater, the fine droplets of sterilising agent can come into contact with the heated surface and receive the energy required for the vaporisation. The operation can take place continuously, as the sterilising agent can be supplied from the supply line outside the vaporising chamber continuously to the nozzle, where the sterilising agent is atomised.

When, after these measures, in the vaporising chamber there is vapour which wants to move further up-stream because of the pre-determined pressure differentials, superheating takes place, beginning directly behind the heated surface of the heater, in a simple manner in that the vapour flows through channels going completely through the heater, and during this flowing receives thermal energy from the hot (heated) walls of said channels. This further receipt of heat in order to super-heat the vapour takes place behind the up-stream surface of the heater, which is the so-called heated surface, as far as the down-stream end surface of the heater, into which the channels finally open out. This is the down-stream side of the heater, in the proximity of which the heating elements are arranged. In this way it is guaranteed that the highest temperature is at the down-stream end of the heater, and the heater contains the greatest amount of heat in this down-stream end area, which begins to migrate towards the up-stream end.

This flow of heat from the down-stream end area to the up-stream surface of the heater ensures, on the one hand, that the desired temperature is obtained on the hot surface and is maintained, and ensures on the other hand an intensive transporting of heat which is necessary because approximately ten times the amount of heat is delivered from the heated surface to the liquid (the droplets) to be vaporised in the channels than in the down-stream end area.

If water is taken as an example, which is to be converted from the liquid to the vapour phase on the heated surface at 100° C., the amount of heat required is then 2257 kJ/kg.

If it is desired that the vapour be heated in the down-stream end for super-heating, only $$2\text{kJ/kg}\times\text{K}$$

is needed per degree Celsius for this super-heating, wherein K is degrees Kelvin.

If it is desired to heat the vapour at 100° C. on the heated surface, good super-heating to approximately 200° C. in the down-stream end area requires a temperature difference of 100° C. Consequently the amount of heat necessary for 100° C. is one hundred times the amount shown hereinabove. This is therefore only 200 kJ/kg, that is to say a tenth of the amount of heat necessary for the vaporising. Because of this a high temperature can build up during operation in the down-stream end area and also be maintained during the super-heating operation.

If it were desired that a yet higher temperature be obtained by means of the super-heating in the down-stream end area, it would be necessary only to lengthen the heater correspondingly, In the case of the example described hereinabove, with a super-heating temperature in the down-stream end area of approximately 200° C., however, a relatively short, compact heater is sufficient.

A practical example for good vaporisation and super-heating of a sterilising agent is obtained with a heater with a diameter of approximately 150 mm and a length of approximately 230 mm.

It is also advantageous according to the invention when the vaporising chamber is connected to a pump or a blower for gaseous carrier material, and widens out towards the heated surface. For example, hot air with a temperature of approximately 150° C. can be used as such a gaseous carrier material. Gases and mist are distributed by means of the pumped-in carrier material and come into intensive contact with the entire heated surface. This produces a good thermal transfer and a good emission of heat in order to obtain rapid and intensive vaporisation. This also happens when the heat channels lead off the heated surface so that the surface is in this way somewhat reduced.

It is advantageous when the heater is formed from a material with good thermal conduction coefficients. Metal has been shown to be advantageous in this case, in particular aluminium.

According to the invention, the heater can also be provided externally with a heat insulating layer. The thermal gradient from the down-stream end area to the up-stream heated surface changes surprisingly little because of this.

In an advantageous further embodiment of the invention, the heater is a solid, cylindrical block of metal, the up-stream surface and the down-stream end surface are planar and provided with holes to which straight, parallel channels are connected, and the vaporising chamber fitted up-stream and the collecting funnel fitted down stream are both configured as funnels widening out towards the planes of the heater. In this way a transport medium supplied through a line with a small diameter can be mixed with another medium supplied from the side from the exterior through a supply line, for example, the sterilising agent, and applied to the entire heated surface, as by means of the funnel-shaped widening the mixture is also conducted onto the outer areas of the heated surface. When, the other way around, a collecting funnel is fitted behind the down-stream end surface, which tapers from the end surface in the down-stream direction, all the vapour streams from the channels can then be focused and collected in a diverter. After flowing through a path length of approximately 1 m, the collecting bottle for the super-heated sterilising agent is envisaged. The super-heating temperature now only needs to be set high enough for the super-heated sterilising agent or the mixture of air with super-heated sterilising agent not to substantially change its phase and as far as possible also its temperature along the path to the storage bottle.

Good results are obtained with a substantially regular flow speed of the vapour found in the super-heating through the channels described. If instead, a five times greater amount of vapour per unit time is desired, the arrangement of five times as many channels is then used. In other words, the total number of channels depends on the volume of vapour flowing through.

Figure 2:
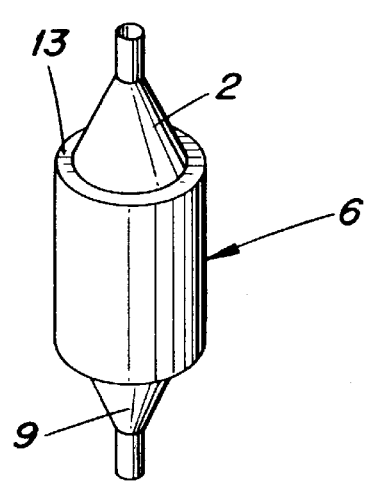
Figures 3, 4:
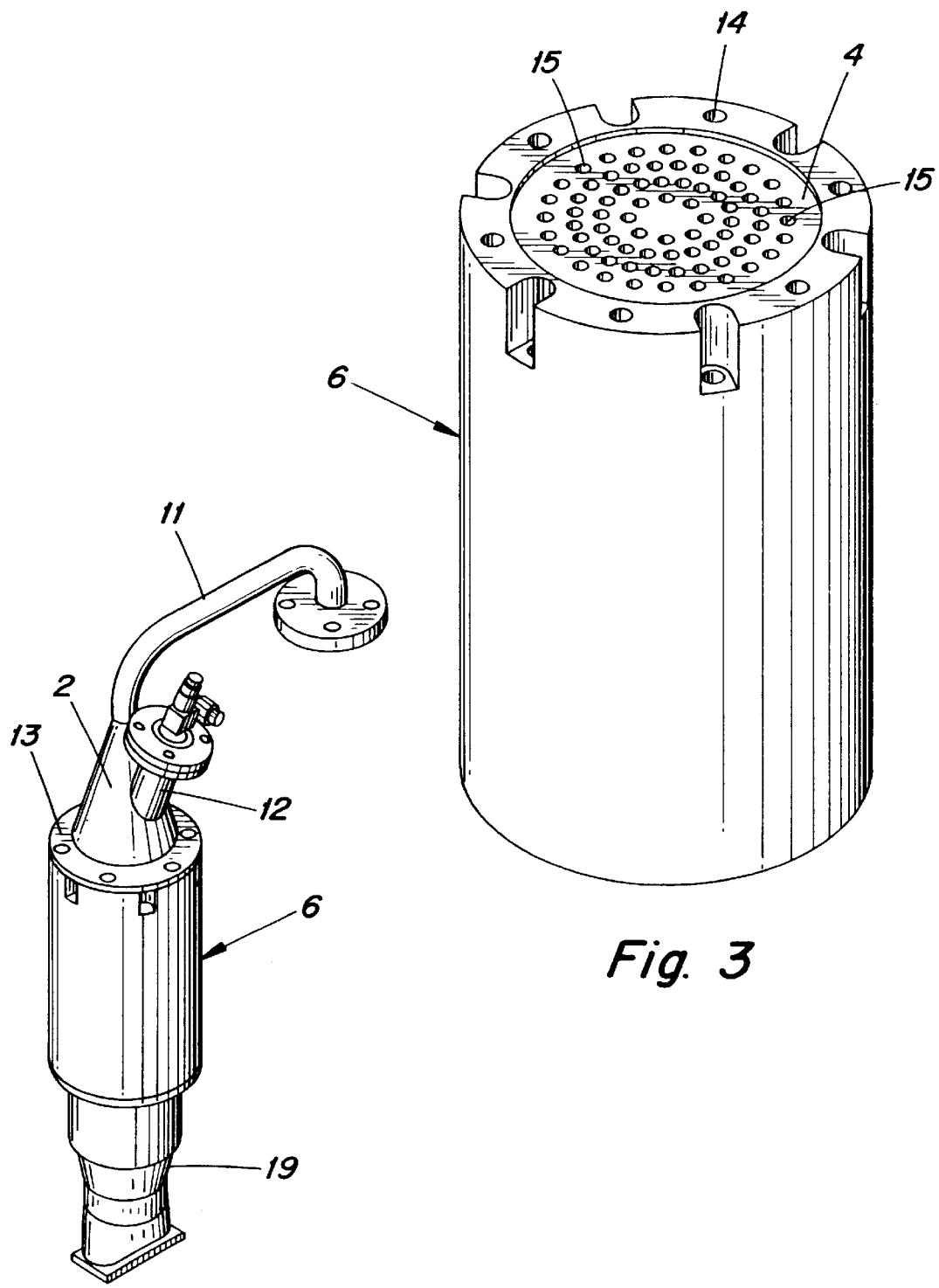
Figure 5:
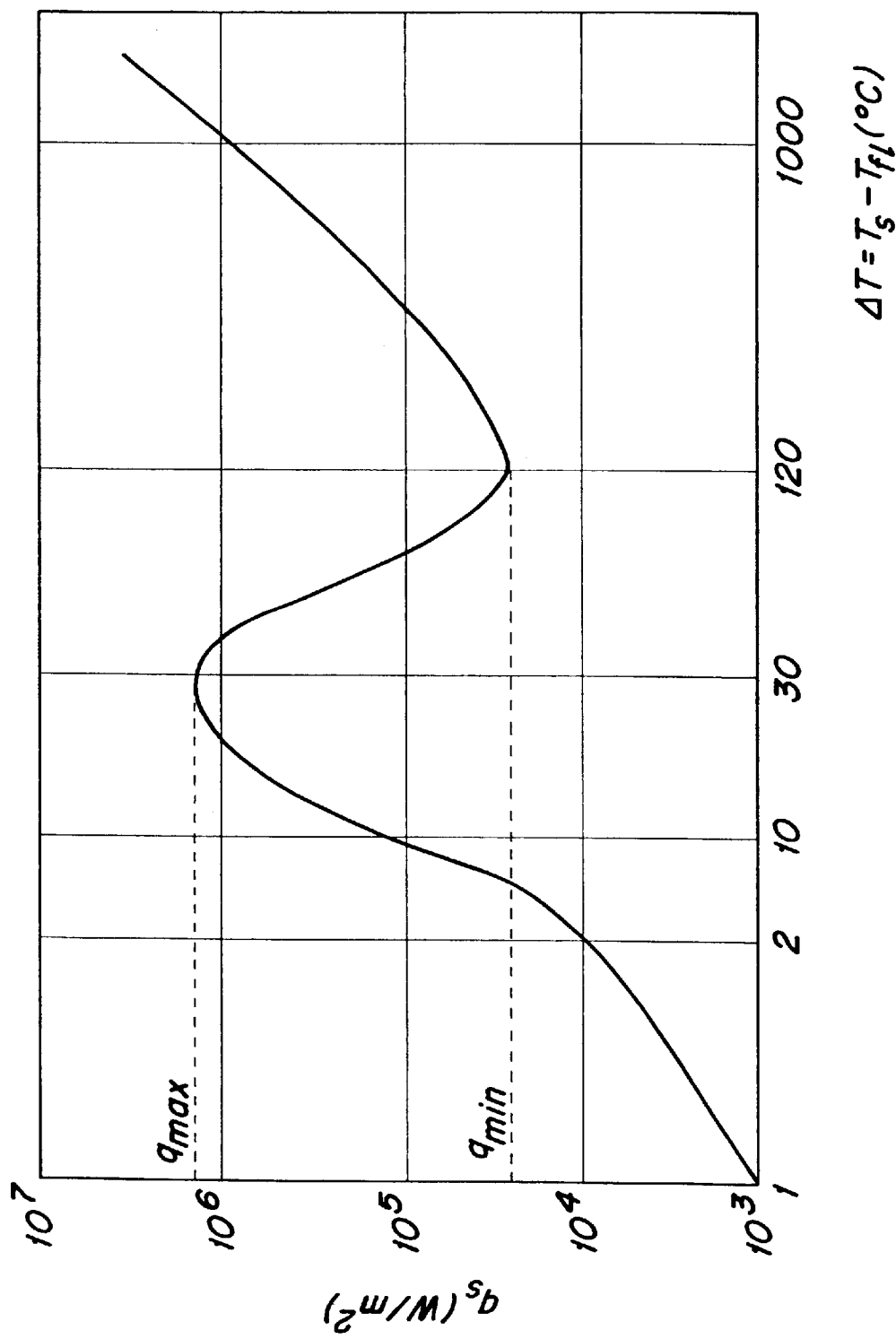

Further advantages, features and possibilities for application of the present invention will be evident from the following description of preferred embodiments with reference to the attached drawings. In these is shown, in:

FIG. 1 the enlarged cross-sectional view of a heater shown schematically in FIG. 2, FIG. 2 isometrically, a simplified and schematic representation of a heater with the vaporising chamber arranged up-stream and the collecting funnel arranged down-stream, FIG. 3 a practical embodiment without the bottle underneath and the supply elements above, FIG. 4 enlarged and isometrically, the representation of another practical embodiment of a heater, and FIG. 5 a diagram representing the boiling curve for water at one atmosphere.

In the simplified embodiment of FIG. 1, hot air is conducted in the direction of the arrow 1 with the aid of pumps which are not shown, via the supply line 11 shown in FIG. 4, into the vaporising chamber 2. The vaporising chamber sits like an inverted funnel on the planar, heated surface 4, the temperature of which is sensed by a sensor labelled 5. A nozzle 3 is located opposite the heated surface 4 approximately in the centre of the funnel-shaped vaporising chamber 2 and is connected to a supply line 12 leading to the outside of the vaporising chamber 2.

FIG. 4 shows that the actual arrangement of the supply line 12 for supplying liquid hydrogen peroxide as the sterilising agent is configured differently and is formed and set at a different angle to the direction of flow 1, assumed here to be vertical.

The vaporising chamber 2 is screwed onto the heater, generally labelled 6, by means of the up-stream flange 13 (FIG. 4), which heater carries screw holes 14 at the top for fixing the flange 13. The up-stream planar surface, that is to say the so-called heated surface 4 of the heater 6, can be seen in FIG. 3 in an inclined plan view as a planar plate with a large number of holes 15.

Straight channels 7 running parallel to each other are connected beneath these holes 15 shown in FIG. 1. They are at a distance apart from one another, as can be seen in the sectional view of the heater 6 in FIG. 1, and terminate in the down-stream end surface 16 of the heater 6. Heaters 8 are set into the outside of the down-stream end area 17 of the heater 6 in the manner of a ring, these being, in the case of the embodiment shown here, electric heating rods, the electrical connecting cable of which is labelled 18.

Below, onto the down-stream end surface 16, which is also a planar plate with holes, there is connected the collecting funnel which widens out in the manner of a truncated cone in the counter flow of the super-heated vapour towards the down-stream end surface 16, and therefore unites the flowing super-heated streams of vapour and guides them in the direction of the arrow 10 through the diverter 19 (FIG. 4), to a collecting bottle connected below, which is not shown.

The diagram of FIG. 5 shows the typical boiling curve for water at one atmosphere. The surface thermal flow $q_s$ in watts per square meter is plotted against the temperature difference $\Delta T$ in degrees Celsius. This temperature difference results from the current temperature minus the temperature of the liquid phase in degrees Celsius. With water, $T_{fl}$ is 100° C. The black curve, the boiling curve for water, shows a first maximum at approximately $T_s$=130° C. From there, with rising temperature which, for example, can be transferred during super-heating to the water vapour, the amount of heat of the water vapour generally decreases to a minimum value $q_{min}$ at approximately 220° C.

If, in the case of the device, for example according to FIG. 1, a flow of heat is desired in the heater 6 counter to the direction of the arrows 1 and 10, that is to say from below to above, then a temperature difference must be established between the down-stream end area 17 of the heater 6 and its heated surface 4. Precisely this occurs when the temperature of the heated surface is set at a range between 130° C. and 140° C., when the vaporisaton and super-heating of hydrogen peroxide or a mixture of air and hydrogen peroxide is desired. During vaporisation, $q_{max}$ is transferred, and during super-heating the comparable amount of heat is kept lower by an order of magnitude so that the desired flow of heat counter to the flow direction of the vapour to be super-heated forms, and is maintained.

With a practical embodiment, 100 g $H_2O_2$ per 1 kg air was used, and this mixture of air and liquid vaporised and subsequently super-heated. According to arrow 1 of FIG. 1, the hot air at 150° C. is pumped in and the hydrogen peroxide is sprayed in a mist through the nozzle 3.

In the down-stream end area 17 of the heater, a temperature of approximately 214° C. was obtained. With these values a mixture of air and super-heated vapour is obtained in the collecting funnel 9, which does not condense on the path through the diverter 19 down in the direction of the arrow 10 as far as the collecting bottle. In the bottle itself, condensation is permissible but not necessary.

What is claimed is:

1. A method for vaporising and super-heating a sterilising agent, which is brought to a first temperature and vaporised with the aid of a heated surface, and the vapour is subsequently brought to a second, higher temperature and super-heated by means of heating elements, wherein
   a) the sterilising agent is sprayed onto the heated surface, which is heated to a first temperature,
   b) which is lower than a surface temperature at which film boiling begins,
   c) the first temperature of the heated surface is sensed and converted into signals for controlling the heating elements for super-heating, and
   d) the sterilising agent vapour is heated in a counter flow such that the first temperature is kept substantially constant by means of the second, higher temperature and by means of a flow of heat directed in the opposite direction to the flow of vapour.

2. Method according to claim 1, wherein the sterilising agent is hydrogen peroxide ($H_2O_2$).

3. Method according to claim 1, wherein the first temperature is in the range of 100° C. to 150° C.

4. Method according to claim 1, wherein a gaseous carrier medium is introduced into the spray stream of sterilising agent.

5. Method according to claim 1, wherein a gaseous carrier medium has a temperature in the range of 130° C. to 170° C.

6. A device for vaporising and super-heating a sterilising agent, in which is brought to a first temperature and vaporised with the aid of a heated surface, and the vapour is subsequently brought to a second, higher temperature and super-heated by means of heating elements, having a vaporising chamber and a heater, super-heating channels and heating elements connected after said vaporising chamber, wherein
   a) the heated surface is an up-stream surface of the heater,
   b) onto which the vaporizing chamber is directly mounted,
   c) a nozzle connected to a supply line leading to an exterior is fitted in the vaporizing chamber, opposite the heated surface,
   d) open, continuous channels are provided from the up-stream surface to a down-stream end surface of the heater, and that
   e) the heating elements are housed in the down-stream end area of the heater.

7. Deceive according to claim 6, wherein the vaporising chamber is connected to a pump or a blower for gaseous carrier material, and widens out towards the heated surface.

8. Device according to claim 6, wherein the heater is formed from a material with a good thermal conduction coefficient.

9. Device according to claim 6, wherein the heater is provided externally with a heat insulating layer.

10. Device according to claim 6, wherein the heater is a solid, cylindrical block of metal, the up-stream surface and the down-stream end surface are planar and provided with holes, to which straight, parallel channels are connected, and that the vaporising chamber connected up-stream and collecting funnel connected down-stream are funnels widening out towards planes of the heater.

11. A device for vaporizing and super-heating a sterilizing agent, comprising:
   a vaporizing chamber for vaporizing the sterilizing agent, the vaporizing chamber being funnel in shape;
   a heater having an upstream surface and a downstream end surface, the upstream surface and the downstream end surface are planar and provided with holes;
   a heated surface is the upstream surface of the heater and is disposed downstream of the vaporizing chamber;
   super-heating channels disposed between holes of the upstream surface of the heater and holes of the downstream end surface of the heater;
   heating elements disposed at the downstream end surface of the heater;
   a collecting funnel connected downstream to the heater, said collecting funnel widening out towards the planes of the heater;
   wherein the sterilizing agent is brought to a first temperature and vaporized with the aid of a heated surface, and the vapor is subsequently brought to a second, higher temperature and super-heated by means of the heating elements.

12. Method according to claim 1, wherein the first temperature is in the range of 120° C. to 140° C.

13. Method according to claim 1, wherein a gaseous carrier medium has a temperature in the range of 120° C. to 160° C.

14. Method according to claim 1, wherein a gaseous carrier medium has a temperature appro